United States Patent
Sanchez et al.

(10) Patent No.: US 9,339,780 B2
(45) Date of Patent: May 17, 2016

(54) DEVICE FOR DISTRIBUTING FEED AND RECOVERING EFFLUENS IN A RADIAL BED CATALYTIC REACTOR

(71) Applicant: IFP Energies Nouvelles, Rueil-Malmaison (FR)

(72) Inventors: Eric Sanchez, Saint Genis Laval (FR); Gilles Ferschneider, Chaponnay (FR); Frederic Bazer-Bachi, Saint Genis-Laval (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 250 days.

(21) Appl. No.: 14/099,451

(22) Filed: Dec. 6, 2013

(65) Prior Publication Data

US 2014/0094634 A1    Apr. 3, 2014

Related U.S. Application Data

(62) Division of application No. 12/845,276, filed on Jul. 28, 2010, now Pat. No. 8,715,584.

(30) Foreign Application Priority Data

Jul. 29, 2009    (FR) ..................................... 09 03720

(51) Int. Cl.

| | |
|---|---|
| *C10G 35/04* | (2006.01) |
| *C07C 6/04* | (2006.01) |
| *B01J 8/00* | (2006.01) |
| *B01J 8/08* | (2006.01) |
| *B01J 8/12* | (2006.01) |
| *C07C 5/27* | (2006.01) |
| *C07C 6/06* | (2006.01) |
| *C10G 35/12* | (2006.01) |

(52) U.S. Cl.

CPC ............... *B01J 8/0015* (2013.01); *B01J 8/003* (2013.01); *B01J 8/0085* (2013.01); *B01J 8/085* (2013.01); *B01J 8/12* (2013.01); *C07C 5/2702* (2013.01); *C07C 5/277* (2013.01); *C07C 6/04* (2013.01); *C07C 6/06* (2013.01); *C10G 35/12* (2013.01); *C10G 2300/104* (2013.01); *C10G 2300/1044* (2013.01); *C10G 2400/02* (2013.01); *C10G 2400/20* (2013.01); *C10G 2400/22* (2013.01)

(58) Field of Classification Search

CPC ...... B01J 8/0214; B01J 8/0278; C10G 35/04; C07C 6/04; C07C 5/277

See application file for complete search history.

(56) References Cited

U.S. PATENT DOCUMENTS 2,417,393 A    3/1947    Evans

FOREIGN PATENT DOCUMENTS

| EP | 0269171 A2 * | 6/1988 | ............ B01J 8/0214 |
|---|---|---|---|
| WO | 03001131 A1 | 1/2003 | |

OTHER PUBLICATIONS

Institut National De La Propriete Industrielle, "Search Report" FR0903720 Applicant: IFP, Mailed Mar. 1, 2010.
Institut National De La Propriete Industrielle, "Written Opinion" FR 0903720 Applicant: IFP, Mailed Mar. 1, 2010.

* cited by examiner

*Primary Examiner* — Randy Boyer
(74) *Attorney, Agent, or Firm* — Millen, White, Zelano, Branigan, P.C.

(57) ABSTRACT

The invention describes a radial bed catalytic conversion unit having an outer cylindrical chamber (1), an inner chamber (2) which is also cylindrical, the annular zone included between the outer chamber and the inner chamber, termed the reaction zone (I), being filled with catalyst under slow gravitational flow, and the feed being introduced via an inlet pipe (E), connected to an intermediate box (F) which is in turn connected to a plurality of distribution tubes (3) disposed inside the reaction zone (I) in the vicinity of the outer chamber (1).

17 Claims, 4 Drawing Sheets

DEVICE FOR DISTRIBUTING FEED AND RECOVERING EFFLUENS IN A RADIAL BED CATALYTIC REACTOR

This application is a divisional of U.S. patent application Ser. No. 12/845,276 (now U.S. Pat. No. 8,715,584).

FIELD OF THE INVENTION

The field of the invention is that of moving bed units with radial circulation of feed and reagents from the periphery of the reaction chamber towards the centre, or from the centre of the reaction chamber towards the periphery. The skilled person defines "radial" as a flow of gaseous reagents occurring through a catalytic bed which is generally moving in a set of directions corresponding to radii orientated from the periphery towards the centre or from the centre towards the periphery.

The unit that is most representative of that type of flow is regenerative reforming of gasoline type hydrocarbon cuts which may be defined as having a distillation range in the range 80° C. to 250° C. However, the field of application of the present invention is broader and the following may be cited in addition: catalytic reforming of gasolines, skeletal isomerization of various C4, C5 olefinic cuts, or the metathesis process for the production of propylene, for example. This list of processes is not exhaustive, and the present invention may be applied to any type of catalytic process with radial flow and gaseous feed. Thus, in the context of novel energy technologies, the ethanol to diesel process, for example, could use this type of technology.

Some radial bed units, including regenerative reforming, use what is termed a moving bed catalyst flow, i.e. slow gravitational flow of particles of catalyst confined in the annular chamber defined by the outer wall of the reactor and an inner wall corresponding to the central collector which recovers the reaction effluents.

More precisely, in that type of radial bed unit, the catalyst bed has an annular shape in that it extends from the outer periphery of the chamber to the inner periphery of said chamber which defines the central collector for collecting the effluents.

The feed is generally introduced via the outer periphery of the annular bed and passes through the catalytic bed in a manner which is substantially perpendicular to the vertical direction of flow of the latter. The reaction effluents are recovered in a central collector.

The present invention consists of a device for introducing feed directly into the annular catalytic bed, and for collecting reaction effluents in a central collector which means that certain problems linked to the current technology can be reduced.

In a variation, the present invention also means that the feed can be introduced via the central pipe and that the reaction effluents can be recovered at the periphery.

Finally, the present invention can substantially improve the efficiency of the unit because the feed distribution system can be repaired easily if damaged; repair simply consists of replacing the damaged distribution tube or tubes, and thus means that the process can operate better.

Examination of the Prior Art

The majority of the reactors used in the oil industry to carry out hydrocarbon reforming reactions or the skeletal isomerization of olefinic cuts are radial reactors. The catalytic bed is in the form of a vertical cylindrical ring delimited on its inner side by an inner screen retaining the catalyst and on the outer side either by another screen of the same type as the inner screen or by a device consisting of an assembly of screen elements in the form of scallops.

That device is essentially intended to facilitate repair operations since it replaces a continuous screen by a series of interchangeable modules.

In the remainder of the text, when the term "outer screen" is used, this will encompass the device constituted by screen elements in the form of scallops.

The inner and outer screens are porous so as to allow passage of the feed into the annular catalytic bed on the outer screen side and passage of reaction effluents into the central collector on the inner screen side.

The gaseous feed enters via the top of the reactor and is distributed in the distribution zone located between the outer wall of the reactor and the outer screen, then traverses the annular catalytic bed in a substantially radial manner.

After traversing the catalytic bed, the reaction effluents are collected in a vertical cylindrical collector through the inner screen retaining the catalyst.

Further, if it is desired to maintain the level of activity of the catalyst, a portion of the used catalyst may be replaced by fresh catalyst. These operations of withdrawing used catalyst and introducing fresh catalyst are carried out in the prior art using withdrawal legs placed at the bottom of the reactor, and introduction legs located in the annular zone between the outer screen and the inner screen.

The catalyst used in the reforming reactors may have various shapes, such as extrudates, beads or others. The diameter or equivalent diameter is generally from 1 mm to 4 mm, and more particularly 1.5 mm to 3 mm. The constraints on producing the contact means of the reactors are in a direct relationship with the physical characteristics of the catalyst.

The problems linked to the gas phase radial bed catalytic reactor technology is essentially that of confinement of the catalyst in the annular zone defined by the outer and inner screens, whatever the operating conditions (in operation, when cooling, heating, or in an emergency stop situation) which could cause large differential dilations linked to the various temperatures of the unit.

Confining the catalyst requires a lot of contact means, with concomitantly severe manufacturing and assembly constraints.

In a certain number of industrial units, problems with mechanical strength have arisen with the outer screen, in particular the phenomenon of buckling of a portion of that screen.

Repairing the screen in question is not easy because of the available working area, and generally requires that the screen be cut up into bits which can pass through the manhole, then to weld new portions of screen. That type of repair immobilizes the unit (and thus it is non-productive) for periods which may be as long as 1 to 2 months.

The present invention essentially consists of replacing the outer screen by a feed distribution device consisting of a plurality of vertical distribution tubes, immersed in the catalytic bed in the vicinity of the external wall of the reactor.

Such a device is also mechanically stronger, meaning that the problems mentioned above can be limited or even eliminated, and thus downtime for the unit can be reduced.

In a variation of the present invention, the bent shape of the vertical feed gas distribution tubes at their lower end contributes to better use of the catalytic volume.

Finally, in a further variation of the present invention, it is possible to reverse the direction of movement of the reagent gases, the feed being introduced via a central pipe, and the effluents being recovered by the device of the invention which then acts as a collecting device.

BRIEF DESCRIPTION OF THE INVENTION

Figure 1:
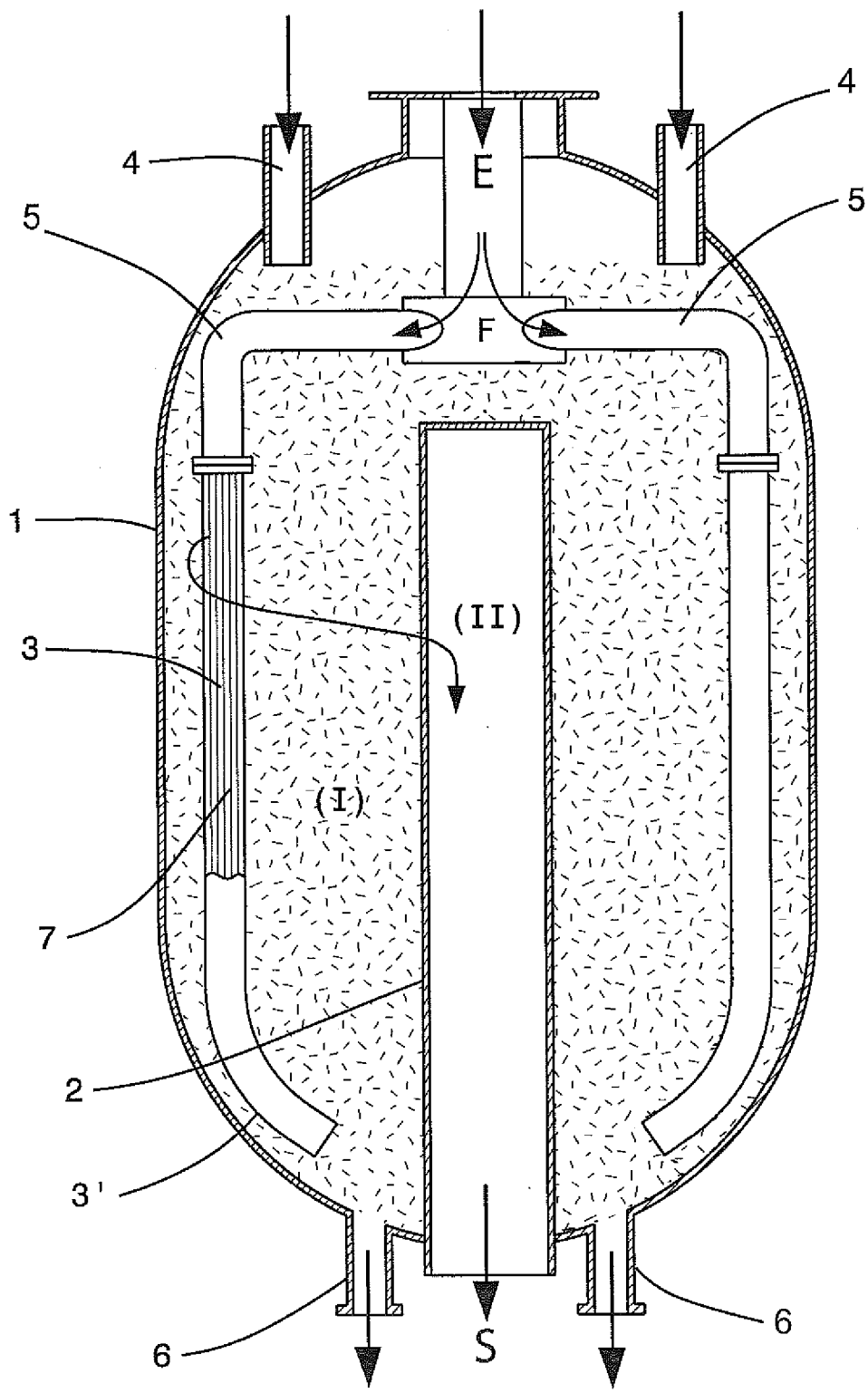
FIG. 1 is a sectional view of the inside of a unit in accordance with the invention which shows the circuit for distribution of feed using vertical tubes immersed in the catalytic bed, and for collecting the reaction effluents via the central collector, as well as the movement of the catalyst using overhead introduction legs, and withdrawal legs at the bottom of the reactor.

The present invention can in general be described as a novel gas phase radial bed catalytic conversion unit using slow gravitational flow of the catalyst. This type of unit has many applications in refining; examples which may be cited are gasoline catalytic reforming, the skeletal isomerization of various C4, C5 or other olefinic cuts, or the metathesis process for the production of propylene or, in a non-exhaustive manner, any moving catalytic system with radial gas flow.

The unit of the present invention has an outer cylindrical chamber 1 and an inner chamber 2, which is also cylindrical, the annular zone included between the outer chamber and the inner chamber, termed the reaction zone I, being filled with catalyst under slow gravitational flow.

The present invention falls into two principal variations which will hereinafter be designated as A) and B).

A) In a first variation of the present invention, the feed is introduced via an inlet pipe B, connected to an intermediate box F which is in turn connected to a plurality of distribution tubes 3 disposed inside the reaction zone I in the vicinity of the outer chamber 1, said distribution tubes being substantially vertical, and extending approximately over the entire height of the reaction zone I.

The term "substantially vertical" means that the tubes may have an inclination in a plane tangential to said tubes of an angle in the range 0 to 15°. The notion of a tangential plane will be defined in more detail below in the detailed description.

The term "extending approximately" means that the vertical length of the tubes is at least 80% of the height of the reaction zone I.

The reaction effluents are collected in the central cylindrical zone II defined by the inner chamber 2, also termed the central collector II.

The catalyst is introduced into the upper portion of the reaction zone I using a plurality of introduction legs 4 opening into the upper portion of the chamber I, and the catalyst is withdrawn by means of a plurality of withdrawal legs 6 located in the lower portion of the reaction zone I.

In a large number of situations, the intermediate box F for distribution of feed is located inside the reaction zone I, but in a variation of the invention, the zone F for distribution of the feed is positioned outside the outer chamber 1, the distribution tubes 3 still being situated inside said outer chamber I.

According to the present invention, the feed distribution tubes 3 may be disposed in one or more rows, which are approximately concentric circumferences. The term "approximately concentric" means that the centres of all of the rows are contained in a circle centred on the centre of the unit with a radius of less than 20 cm.

In the case in which the feed distribution tubes 3 are disposed about a circumference in a single row, said circumference is located at a distance Dp with respect to the outer chamber 1 of the reaction zone I, said distance Dp being in the range Dt to 0.5 Ep, Dt being the diameter of a tube 3 and Ep being the thickness of the bed in the catalytic zone, and preferably between 1.5 Dt and <4 Dt. The thickness Ep of the catalytic bed is precisely defined as the difference between the radius of the outer chamber 1 and the radius of the central collector II;

In the case in which the distribution tubes 3 are distributed over a plurality of concentric rows, each row corresponding to a circumference, the distance Dr between two consecutive rows is in the range 1.5 Dt to 4 Dt.

In accordance with a particular characteristic of the present invention, the centre to centre distance (Dc) separating two consecutive distribution tubes 3 is such that the angle $\phi$ formed by the radii passing through the centre of the tube and the centre of the unit has a value in the range 5° to 90°, preferably in the range 10° to 30°.

In accordance with another particular characteristic of the present invention, the angular sector for distribution of feed over a distribution tube 3 is orientated towards the wall of the outer chamber 1 with an angle of opening a in the range 30° to 360°, preferably in the range 30° to 180°.

In accordance with another particular characteristic of the present invention, the angular sector for distribution of the feed distribution tubes 3 is formed by a Johnson screen.

In accordance with a particular characteristic of the present invention, the distribution sector of the feed distribution tubes 3 is formed by orifices distributed at the wall of said sector, the diameter of the orifices being in the range 0.3 to 0.8 dp, dp designating the equivalent diameter of the catalyst grains.

The term "equivalent diameter" means the diameter that conserves the ratio of the surface area to the volume of the catalyst particles.

In accordance with one particular characteristic of the present invention, the lower end of the distribution tubes 3 is bent so that it penetrates into the lower dished portion of the reaction zone I, thereby closely following the shape of the dished bottom.

In accordance with a particular characteristic of the present invention, the distribution tubes 3 may have an angle of inclination with respect to the vertical in a plane termed "tangential" to said tubes, the angle of inclination being in the range 0° to 15°. The term "tangential plane" of a distribution tube 3 is applied to the plane passing through said tube and perpendicular to the radius (Rt) connecting said tube to the central axis of the unit.

Other particular characteristics of the unit will be given in the detailed description.

B) According to a second variation of the present invention, the feed is introduced via a central pipe E extending inside the reaction chamber I, the reaction effluents being collected via a plurality of collecting tubes 3 disposed inside the reaction zone I in the vicinity of the outer chamber 1, said collecting tubes 3 being substantially vertical and extending substantially over the entire height of the reaction zone, and being connected to a collection zone F connected to the effluent outlet pipe S. The collection zone F may thus be either inside the reaction zone, or possibly outside said zone. Catalyst is introduced into the upper portion of the reaction zone I using a plurality of introduction legs 4 opening into the upper portion of the chamber I, and catalyst is withdrawn via a plurality of withdrawal legs 6 located in the lower portion of the reaction zone.

The catalytic conversion unit of the present application may be applied to all variations of processes such as catalytic gasoline reforming, skeletal olefin isomerization, possibly the metathesis process for the production of propylene, and possibly to oligocracking processes, as well as for the process for transformation of ethanol into a base for a diesel fuel, for example.

In general, the field of application of the unit of the present invention is that of units with a radial flow of gas and slow gravitational flow of catalyst.

DETAILED DESCRIPTION OF THE INVENTION

In the prior art configuration of radial bed reactors, the distribution of the feed in the annular zone included between the outer wall of the reactor and the outer screen suffers from many problems. The catalyst has to be confined in this zone during the various heating/cooling operational phases and emergency stoppages of the unit. Because of the metals used and the manufacturing and assembly tolerances, there are considerable constraints on the arrangement of the contact means in the reactor in order to limit possible leaks of catalyst on the gas distribution side, between the outer wall of the reactor and the outer screen.

In order to overcome these problems, the present invention means that the contact means of radial bed reactors can be simplified and the outer screen can be replaced by a peripheral gas distribution device constituted by a plurality of substantially vertical, parallel tubes with a radial gas distribution sector. The catalyst is thus confined directly between the outer wall of the reactor and the inner screen communicating with the central collector.

Figure 2:
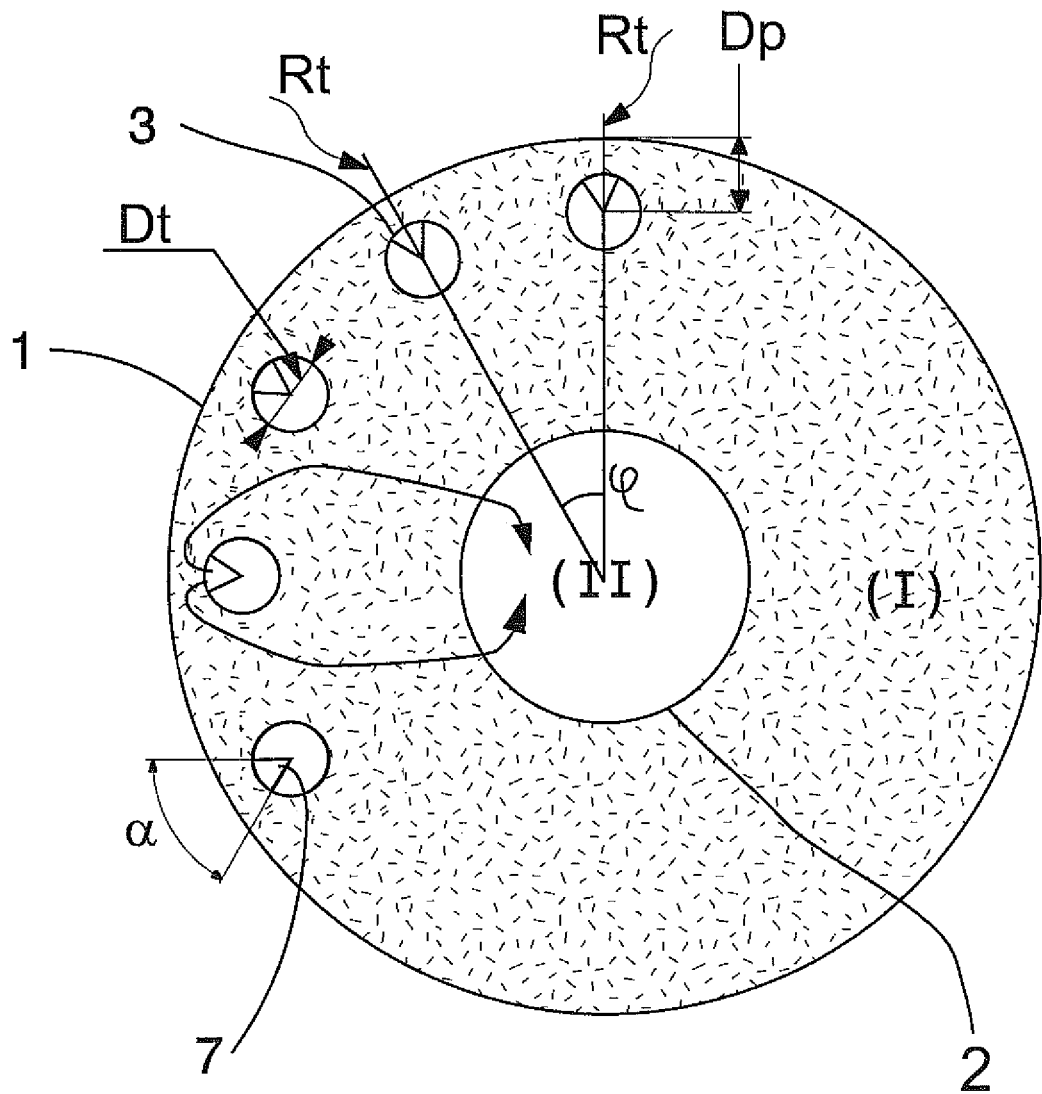
FIG. 2 is a sectional top view of the unit which shows the various tube/wall distances, inter-tube distance, and various angles acting to define the unit.
Figure 3:
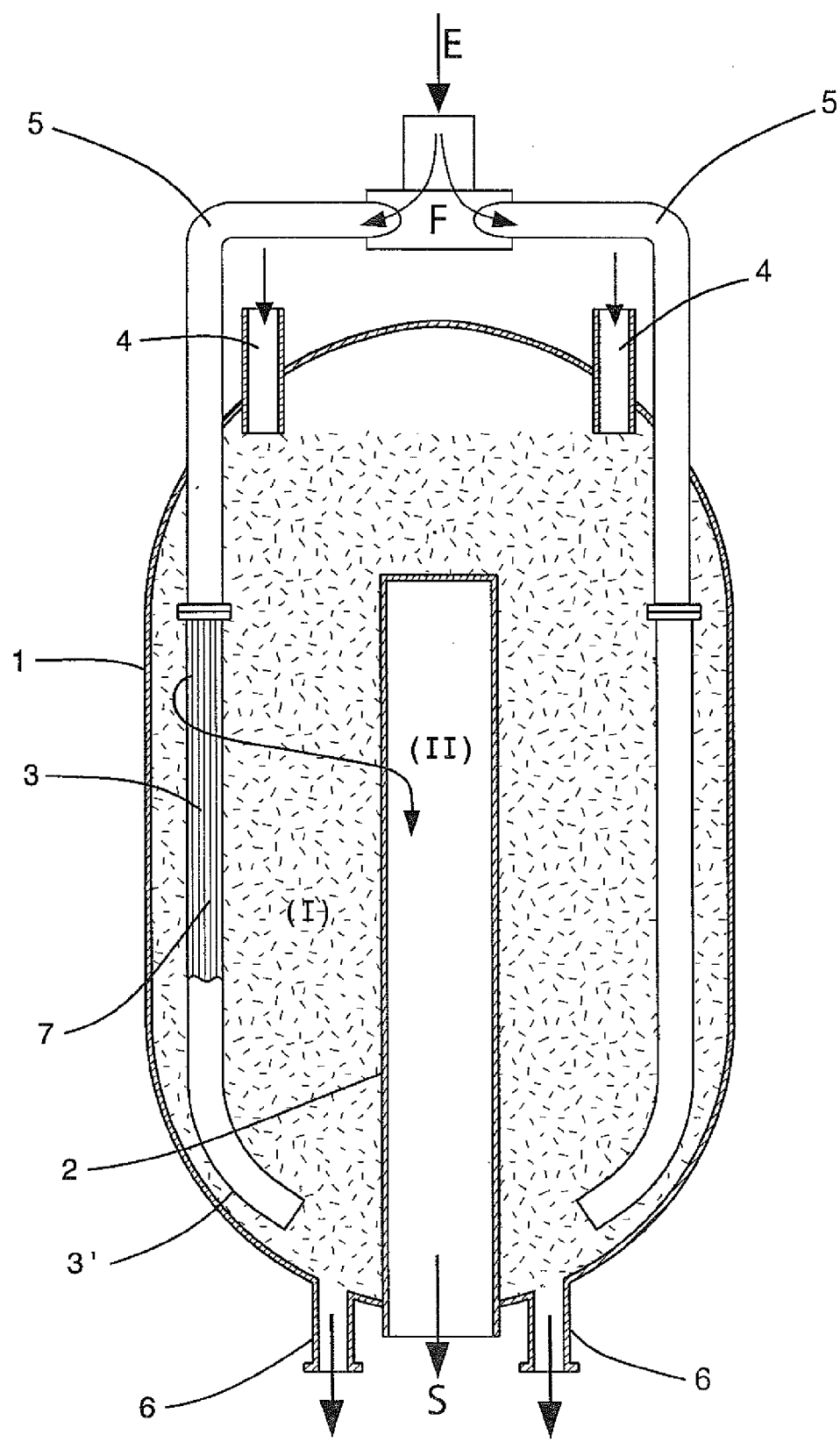
FIG. 3 is a view of a variation of the present invention in which a portion of the feed introduction device is transferred to the outside of the unit.

The remainder of the description is made with reference to FIGS. 1, 2 and 3.

The gaseous feed is introduced into the catalytic bed I via a system of vertical tubes 3 having a well defined internal angular sector, perforations which are distributed in a regular manner, or wall elements constituted by screens generally denoted a "Johnson" screen. The term "Johnson" screen means a screen with lines that are evenly orientated in a given direction, the rigidity being assured by bars running transversely to the lines.

The gaseous feed is introduced into the reactor via a central pipe E, connected to an intermediate box F about which the substantially vertical distribution tubes 3 are distributed.

The term "substantially" should be understood to mean corresponding to a possibility of an inclination of the tubes 3 in a plane tangential to said tube at an angle which may be up to 15°. The expression "tangential plane" should in turn be understood to define a plane such that the distance from the tube to the outer wall of the reactor remains constant.

The intermediate box F may take several forms; the only constraint is that it must communicate with the central pipe E and also with the substantially vertical tubes 3.

With simple, approximately horizontal tube elements, the collector may have a toroidal shape, or be a cylindrical box that receives the pipe E at its centre and from which the substantially vertical tubes 3 disperse. The present invention is compatible with any shape of the intermediate box F; in some cases, it may be inclined with respect to the horizontal, in particular in order to satisfy spatial constraints.

The vertical or slightly inclined tubes 3 may have a cylindrical cross section or an elliptical cross section or even be multilobed, i.e. have several lobes. All tube cross sections are compatible with the present invention.

The catalyst generally moves as a moving bed, i.e. in a gravitational manner at relatively slow speeds of the order of one meter per hour, in the annular zone I included between the outer wall 1 of the reactor and the wall of the collector 2.

The catalyst can thus move around the feed distribution tubes 3.

The catalyst is introduced into the annular zone I via introduction legs 4 located in the upper portion of the reactor, and the catalyst is withdrawn from the annular zone I via the withdrawal legs 6 located in the lower portion of the reactor.

The device for distribution of feed via the substantially vertical tubes 3 is also optimized in order to obtain the best use of the catalytic bed.

To this end, the distribution tubes 3 may be inclined to a greater or lesser extent at the bottom of the reactor, or even bent along a portion 3' in order to utilize the reaction volume at the reactor bottom to the best extent.

FIG. 2 shows a sectional view of the reactor showing the disposition of the distribution tubes 3 in the vicinity of the outer wall 1 of the reactor, as well as the position of the central collector 2.

The distribution tubes 3 are generally disposed along a circumference located at a distance Dp with respect to the outer wall 1 of the reactor, but may also be aligned along a plurality of concentric circumferences which are then separated by this same distance Dp plus or minus 15%.

In the case in which the feed distribution tubes 3 are disposed along a circumference in a single row, said circumference is located at a distance Dp with respect to the outer chamber 1 of the reaction zone I, said distance Dp being in the range Dt to 0.5 Ep, wherein Dt is the diameter of a tube 3, and Ep is the thickness of the bed of the catalytic zone, preferably in the range 1.5 Dt to 4 Dt. The thickness Ep of the catalytic bed is precisely defined as the difference between the radius of the outer chamber 1 and the radius of the central collector 2.

In the case in which the distribution tubes 3 are distributed in a plurality of concentric rows, each row corresponding to one circumference, the distance Dr between two consecutive rows is in the range 1.5 Dt to 4 Dt.

In a given row, the distance Dc separating two consecutive tubes (known as the centre to centre distance) is such that the angle φ formed by the radii Rt passing through the centre of the tube and the centre of the unit has a value in the range 5° to 90°, preferably in the range 10° to 30°. In the case in which the tubes 3 are distributed over a plurality of rows, the angle φ when passing from one row to the next row may be offset by a value of approximately φ/2, plus or minus 15%.

Each tube has a distribution sector 7 with angle α. This distribution sector 7 extends over the major portion of the vertical length of each tube 3. The term "major portion" means a portion corresponding to at least 80% of the vertical length of the tube 3, and preferably at least 90% of said length.

The angle α is in the range 30° and 360°, and preferably in the range 30° to 180°.

The position of this distribution sector is such that it is symmetrically orientated towards the outer wall 1 of the reactor. The term "symmetrically orientated" means that the distribution sector is orientated towards the outer wall 1 of the reactor, and is divided into two equal half angles either side of the radius Rt connecting the centre of the reactor to the tube concerned (denoted Rt in FIG. 2).

The distribution sector 7 may simply be constituted by perforations made on said sector at the wall of the vertical tube 3, or be constituted by a Johnson screen wall element.

Each tube 3 has a distribution sector 7, and all of the sectors 7 are orientated towards the outer wall of the reactor.

In the particular case in which the distribution sector is open over its whole circumference (i.e. where the angle α is equal to 360°), the distribution in said sector is non-homogeneous in the sense that the half sector orientated towards the wall 1 of the unit has a degree of opening strictly greater than that of the half sector orientated towards the central collector 2.

According to a variation of the present invention shown in FIG. 3, the intermediate box F is located outside the reactor. The distribution tubes 3 then pass through the wall of the outer chamber 1, generally at the upper domed portion.

This disposition means that the catalytic volume of the reaction zone I can be better used, as the portion of the tubes 3 open to the distribution by the angular sector 7 may then exceed 90% of the length of said tubes.

Figure 4:
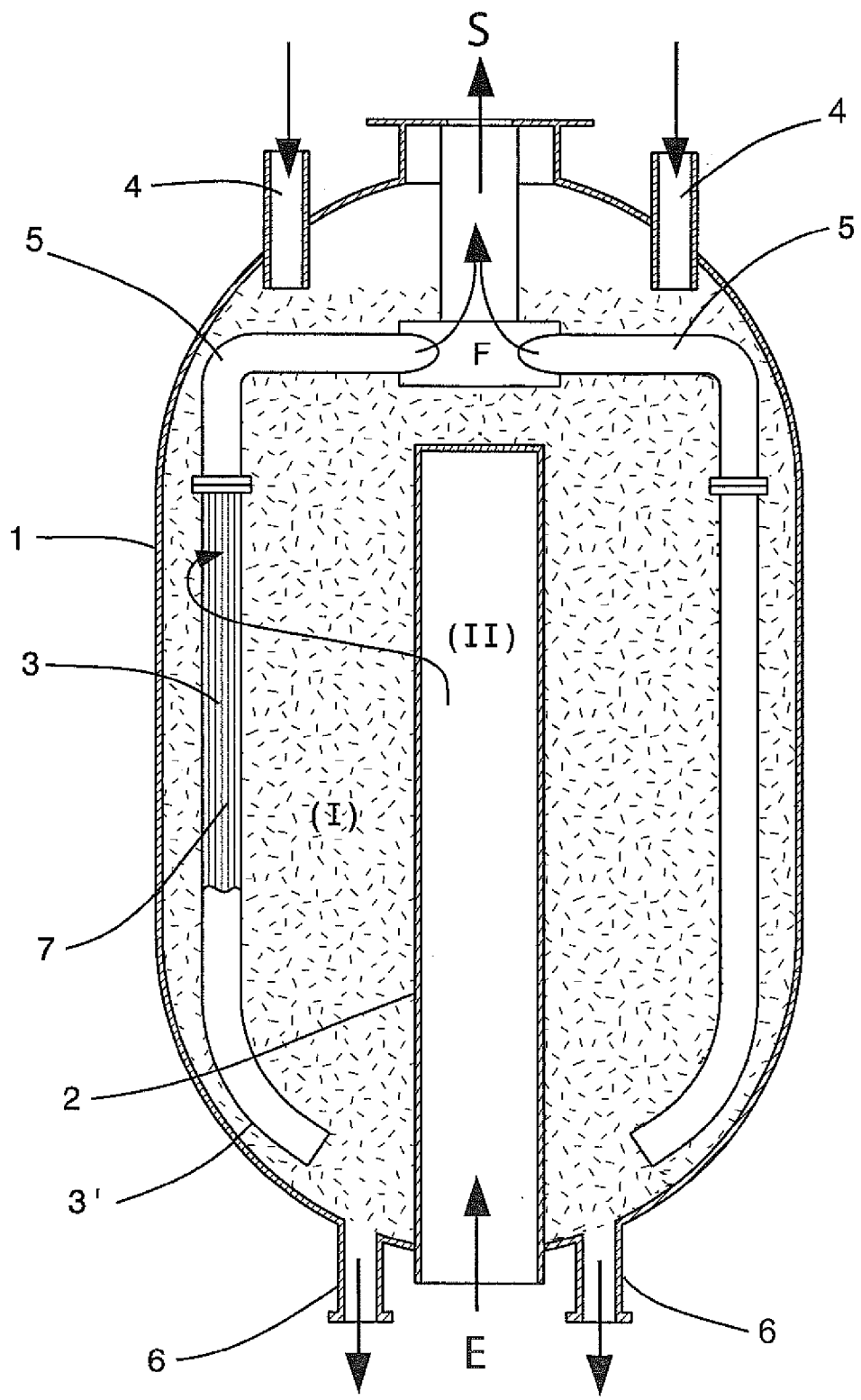
FIG. 4 is a sectional view of the inside of the unit in accordance with a variation of the invention, in which the feed is introduced via the central pipe, and the effluents are collected by the plurality of tubes located at the periphery of the outer chamber of said unit.

According to a variation of the present invention, shown in FIG. 4, it is possible to modify the movement of the gaseous feed by introducing it via the central collector II then by recovering the reaction effluents via the tubes 3 which then become the collector tubes.

FIG. 4 keeps the same numeration for elements with an identical structure although their function has changed. This is the case with the central collector II which becomes the distributor in the present variation.

The effluents thus leave the reactor via the intermediate box F connected to the outlet pipe S. In FIG. 4, the feed is introduced into the bottom of the central collector II, but the invention also encompasses the case in which the feed would be introduced via the top of said central collector II, the lower end thereof then being closed.

The present invention substantially improves the efficiency of the unit by allowing easy repair of the feed distribution system in the case of damage; such a repair then consists of simply replacing the damaged distribution tube or tubes 3, and thus means that the process for which the present unit is used can be operated in an improved manner.

EXAMPLE

The following examples allow a better evaluation of the gain expected with the novel distribution system.

In all cases (prior art or in accordance with the invention), the unit was a regenerative gasoline reforming unit constituted by 4 reactors in series, denoted R1, R2, R3 and R4. The feed was introduced to the head of reactor R1, the effluents from the reactor R1 were introduced to the head of the reactor R2 and so on. The final reaction effluents were recovered at the outlet from reactor R4.

Reactors R1, R2, R3 and R4 operated at decreasing pressures, in the range from 2 bars to 1 bar absolute (1 bar=$10^5$ Pascals).

This unit treated a flow rate of 150 T/h, the feed being constituted by a gasoline cut with a distillation range in the range 80° C. to 250° C.

The catalyst was a platinum-based catalyst deposited on a silica-alumina support which was in the form of spherical beads with a 2 mm diameter.

The feed, vaporized in a furnace located upstream of said unit, was introduced in the gaseous state.

The dimensions compared with prior art reactors and in accordance with the invention are given in the tables below.

The performances of the unit were identical for the prior art and in accordance with the invention. Only the dimensions of the reactors were different.

Prior Art Unit:

The prior art unit was a unit for catalytic reforming of gasolines containing 4 reactors denoted R1, R2, R3 and R4. Each of reactors R1, R2, R3 and R4 was a prior art radial flow reactor, i.e. with feed distribution ensured by an outer screen placed at the periphery of the reaction chamber. The diameter of the central collector was 1150 mm.

Table 1 below shows the dimensions of each of the reactors and the corresponding catalytic volumes.

TABLE 1

| Reactor | Reactor diameter | Outer screen diameter | Total height | Total catalytic volume | Useful catalytic volume |
|---|---|---|---|---|---|
| Reactor 1 | 2.6 | 2.1 | 5.5 | 15.7 | 12.2 |
| Reactor 2 | 2.6 | 2.1 | 5.5 | 15.7 | 12.2 |
| Reactor 3 | 2.85 | 2.35 | 6.9 | 25.9 | 20.8 |
| Reactor 4 | 3.3 | 2.7 | 8.7 | 44.2 | 35.4 |

Unit in Accordance with the Invention

The unit in accordance with the invention comprises 4 reactors R1, R2, R3 and R4 with dimensions identical to those of reactors R1, R2, R3 and R4 of the prior art.

The feed distribution was ensured by a set of 24 tubes 100 mm in diameter, distributed in a single distribution row, said row being located at a distance Dp of 300 mm with respect to the wall of the outer chamber 1 of each of the reactors.

TABLE 2

| Reactor | Reactor diameter | Total height | Total catalytic volume | Useful catalytic volume |
|---|---|---|---|---|
| Reactor 1 | 2.6 | 5.5 | 24.5 | 23.1 |
| Reactor 2 | 2.6 | 5.5 | 24.5 | 23.1 |
| Reactor 3 | 2.85 | 6.9 | 38 | 36.4 |
| Reactor 4 | 3.3 | 8.7 | 64 | 62.2 |

A comparison between Tables 1 (in accordance with the prior art) and 2 (in accordance with the invention) shows that the total catalytic volume (and thus useful volume) increased by approximately 80% for iso-external dimensions of the reactors.

The second example is intended to demonstrate that the present invention can reduce the size of the reactors for a given volume of catalyst with respect to the prior art.

The unit still comprised 4 reactors and distribution of the feed was ensured by a set of 24 tubes 100 mm in diameter, distributed in a single distribution row, said row being located at a distance Dp of 300 mm with respect to the wall of the outer chamber 1 of each of the reactors.

TABLE 3

| Reactor | Reactor diameter | Total height | Total catalytic volume | Useful catalytic volume |
|---|---|---|---|---|
| Reactor 1 | 2.09 | 5.5 | 13.4 | 12.2 |
| Reactor 2 | 2.09 | 5.5 | 13.4 | 12.2 |
| Reactor 3 | 2.32 | 6.9 | 22.3 | 20.8 |
| Reactor 4 | 2.65 | 8.7 | 37.2 | 35.4 |

A comparison between Tables 1 (prior art) and 3 (in accordance with the invention) shows that for a medium capacity unit, the diameter of the reactors can be reduced by more than 20% for the same useful catalytic volume.

The preceding examples can be repeated with similar success by substituting the generically or specifically described reactants and/or operating conditions of this invention for those used in the preceding examples.

In the foregoing and in the examples and, all parts and percentages are by weight, unless otherwise indicated.

The entire disclosures of all applications, patents and publications, cited herein and of corresponding FR application No. 09/03.720, filed Jul. 29, 2009 are incorporated by reference herein.

The invention claimed is:

1. A radial bed catalytic conversion unit comprising:
an outer cylindrical chamber (1), and an inner cylindrical chamber (2) defining an annular zone between the outer chamber and the inner chamber, termed the reaction zone (I), being fillable with catalyst particles under slow gravitational flow, a central pipe (E) extending inside the reaction chamber (I) for introducing feed, a plurality of collecting tubes (3) disposed inside the reaction zone (I) in the vicinity of the outer chamber (1) for collecting effluents, said collecting tubes (3) being substantially vertical and extending over substantially the entire height of the reaction zone and being connected to a collection box (F) within the reaction zone (I), said collection box (F) being connected to an effluent outlet pipe (S), a plurality of introduction legs (4) located in the upper portion of the reaction zone (I) for introducing catalyst particles into an upper portion of the reaction zone (I), and a plurality of withdrawal legs (6) located in the lower portion of the reaction zone (I) for withdrawing catalyst.

2. In a process comprising conducting catalytic reforming of gasolines the improvement comprising conducting the process solely in a radial bed catalytic conversion unit according to claim 1.

3. A process for the skeletal isomerization of C5 cuts, comprising conducting the process solely in a radial bed catalytic conversion unit according to claim 1.

4. A radial bed catalytic conversion unit according to claim 1, wherein tubes (3) for collecting the feed are disposed along a circumference in a single row, said circumference being located at a distance Dp with respect to the outer chamber (1) of the reaction zone (I), said distance Dp being in the range of Dt to 0.5 Ep, wherein Dt is the diameter of a tube (3) and Ep is the thickness of the catalytic zone bed.

5. A radial bed catalytic conversion unit according to claim 1, wherein tubes (3) for distributing the feed are disposed in a plurality of rows, each row corresponding to a circumference, and the distance Dr between two consecutive rows is in the range of 1.5 Dt to 4 Dt, wherein Dt is the diameter of a tube (3).

6. A radial bed catalytic conversion unit according to claim 1, wherein the distance Dc between two consecutive tubes of the same row of said plurality of collecting tubes (3) is such that the angle $\phi$ formed by the radii passing via the center of the tube and the center of the unit has a value in the range of 5° to 90°.

7. A radial bed catalytic conversion unit according to claim 1, wherein an angular sector (7) of a collecting tube (3) for collecting reactants is orientated towards the wall of the outer chamber (1) with an angle of opening a in the range of 30° to 360°.

8. A radial bed catalytic conversion unit according to claim 6, wherein, when the angle of opening a of a distribution sector (7) of a collecting tube (3) is equal to 360°, the distribution within said sector is non-homogeneous such that a half-sector oriented towards the wall (1) of the unit has a degree of opening that is strictly larger than that of a half-sector orientated towards the central collector (2).

9. A radial bed catalytic conversion unit according to claim 1, wherein an angular sector of distribution (7) of the tubes (3) for collecting the reactants comprises a "Johnson" type screen or equivalent.

10. A radial bed catalytic conversion unit according to claim 1, wherein a distribution sector (7) of the tubes (3) for collecting the reactants comprises orifices distributed around the wall of said sector, the diameter of the orifices being in the range of 0.3 to 0.8 dp, wherein dp is the equivalent diameter of the catalyst particles.

11. A radial bed catalytic conversion unit according to claim 1, wherein the lower end of the distribution tubes (3) is curved inwardly into the dished lower portion of the reaction zone (I), following the shape of the dished bottom.

12. In a process comprising conducting catalytic reforming of gasolines the improvement comprising conducting the process solely in a radial bed catalytic conversion unit according to claim 1.

13. A process for the skeletal isomerization of C5 cuts, comprising conducting the process solely in a radial bed catalytic conversion unit according to claim 1.

14. A metathesis process for the production of propylene, comprising conducting the process solely in a radial bed catalytic conversion unit according to claim 1.

15. A radial bed catalytic conversion unit according to claim 6, wherein said angle $\phi$ has a value in the range of 10° to 30°.

16. A radial bed catalytic conversion unit according to claim 7, wherein said angle $\alpha$ is in the range of 30° to 180°.

17. A radial bed catalyst conversion unit according to claim 1, further comprising said catalyst particles.

* * * * *